(12) United States Patent
Grubb et al.

(10) Patent No.: US 7,871,624 B2
(45) Date of Patent: Jan. 18, 2011

(54) CHIMERAL POLYPEPTIDE COMPOSITION FOR CROSS-PLACENTA DELIVERY

(75) Inventors: Jeffrey H. Grubb, St. Louis, MO (US); William S. Sly, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 11/769,693

(22) Filed: Jun. 27, 2007

(65) Prior Publication Data

US 2008/0025995 A1    Jan. 31, 2008

Related U.S. Application Data

(60) Provisional application No. 60/805,954, filed on Jun. 27, 2006.

(51) Int. Cl.
 *A61K 39/00* (2006.01)
(52) U.S. Cl. ............... 424/185.1; 424/134.1; 424/192.1
(58) Field of Classification Search ........................ None
 See application file for complete search history.

(56) References Cited

U.S. PATENT DOCUMENTS

| | | | |
|---|---|---|---|
| 5,580,859 A * | 12/1996 | Felgner et al. ............ | 514/44 R |
| 5,929,304 A * | 7/1999 | Radin et al. ................. | 800/288 |
| 6,359,054 B1 * | 3/2002 | Lemieux et al. ............. | 524/505 |
| 6,475,486 B1 * | 11/2002 | Kolar et al. .............. | 424/130.1 |
| 2004/0005309 A1* | 1/2004 | LeBowitz et al. ........ | 424/94.61 |

FOREIGN PATENT DOCUMENTS

WO    WO 01/36603 A2 *    5/2001

OTHER PUBLICATIONS

Becker et al., Eur J Nucl Med, 1989, 15:361-366, abstract only.*
Ashkenazi et al., Curr Opin Immunol. Apr. 1997; 9:195-200.*
Grubb et al., Proc Natl Aced Sci U S A. Jun 17, 2008;105(24):8375-80. Epub Jun. 10, 2008.*

* cited by examiner

*Primary Examiner*—Michael Szperka
(74) *Attorney, Agent, or Firm*—Mark E. Stallion; Husch Blackwell LLP

(57) ABSTRACT

The invention is directed to chimeral fusion proteins having an IgG1 antibody Fc portion and a lysosomal storage enzyme, particularly a Fc-GUS fusion protein useful in treating Sly's disease in an embryo or fetus. The invention is also directed to methods of treating in born errors of metabolism, particularly Sly's disease, in a fetus by delivering to a pregnant mother a Fc-MPS emzyme fusion protein.

4 Claims, 4 Drawing Sheets

Fig. 1. GUS-Fc Constructs In Mammalian Expression Vector pCXN

Fig. 2. SDS-PAGE of Purified GUS and GUS-Fc
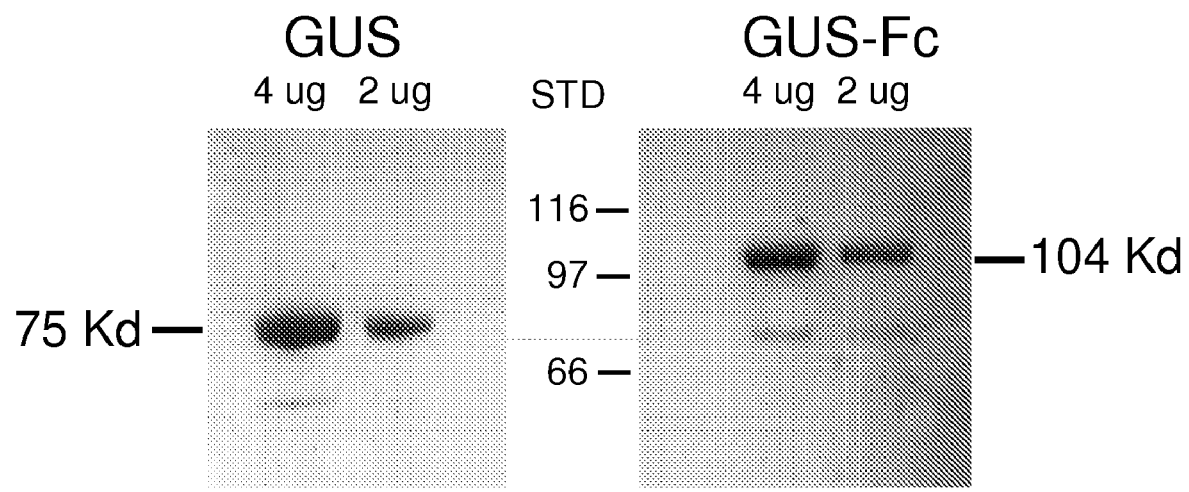

Fig. 3. Clearance of Infused GUSB, GUSB-Fc or Periodate Treated GUS B From the Plasma of MR+/+ or MR -/- Mice
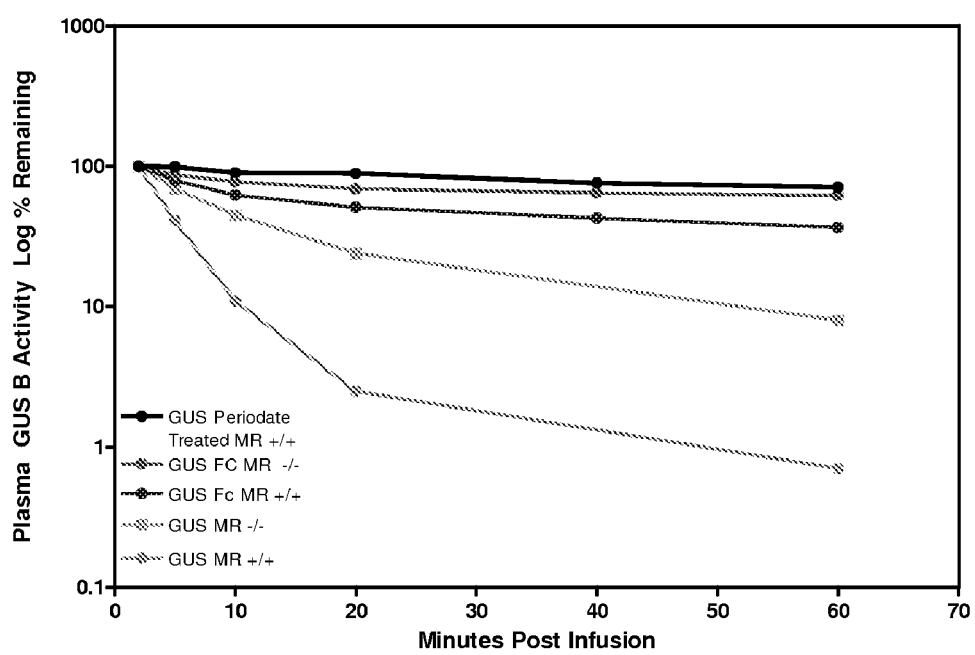

Fig. 4. Clearance of Storage In Tissues From Pups Delivered From Moms Infused With GUS-Fc On Embryonic Days 17 and 18
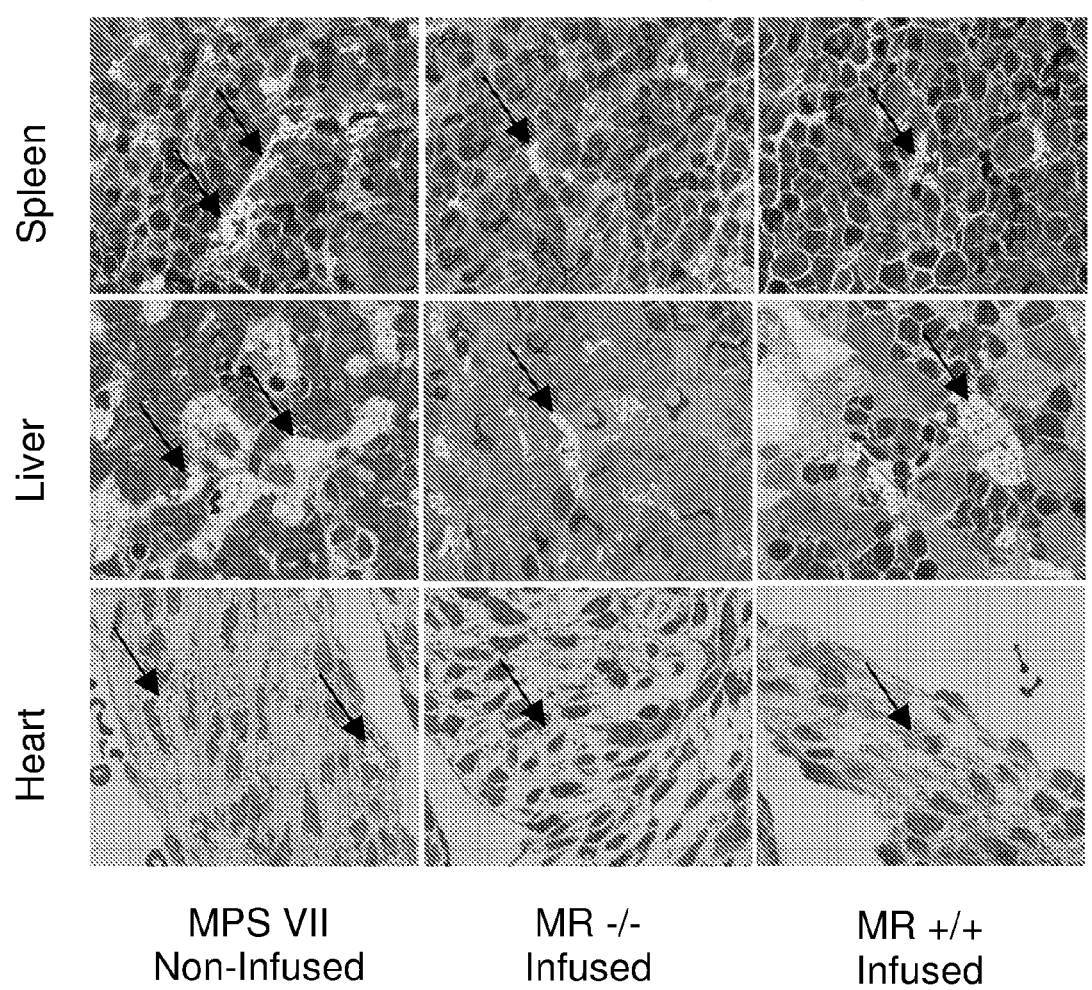

CHIMERAL POLYPEPTIDE COMPOSITION FOR CROSS-PLACENTA DELIVERY

CROSS-REFERENCE TO RELATED APPLICATIONS

This application for patent claims priority to U.S. Provisional Patent Application No. 60/805,954, which was filed on 27 Jun. 2006.

REFERENCE TO SEQUENCE LISTING

This application contains a Sequence Listing in paper and computer readable form which are hereby incorporated by reference in their entireity. The nucleic and amino acid sequences listed in the Sequence Listing are shown using standard letter abbreviations for nucleotide bases, and three letter code for amino acids. Only one strand of each nucleic acid sequence is shown, but the complementary strand is understood as included by any reference to the displayed strand.

FIELD OF THE INVENTION

The invention is directed to pharmacological therapeutics comprising chimeral polypeptides, particularly antibody fragment Fc-MPS enzymes fusions.

BACKGROUND OF THE INVENTION

Recent advances in the medical arts have enabled enzyme replacement therapies (ERTs) for a number of metabolic diseases, especially lysosomal storage diseases (LSDs). Those diseases include Gaucher, Krabbe, Fabry and Pompe diseases, as well as various mucopolysaccharidoses (MPS). Of the MPS diseases, enzyme replacement therapies are currently available or under development for MPS I (Hurler Syndrome), MPS II Hunter Syndrome, MPS IV (Morquio Syndrome), MPS VI (Maroteaux-Lamy Syndrome), and MPS VII (Sly Syndrome). For a review on ERT and LSD, see Brady, R. O., "Enzyme Replacement for Lysosomal Disease," Annu. Rev. Med., 57: 283-296, 2006, which is incorporated herein by reference.

Some MPS disorders, including for example MPS VII, show evidence that significant storage of glycosaminoglycans has already begun in prenatal life (1). In fact, one of the most common manifestations of human MPS VII may be prenatal/neonatal hydrops resulting from beta-glucuronidase (GUS) deficiency in utero (2).

Maternal IgG is known to be transported across the placenta into the fetal circulation by the neonatal Fc receptor (FcRn) (3). This receptor recognizes the Fc domain of the IgG molecule and mediates transcytosis from maternal to fetal circulation.

REFERENCES

The following references are cited throughout this disclosure and are incorporated herein by reference. Applicants reserve the right to challenge the veracity of any statements therein made.

1. Neufeld, E. F. & Muenzer, J. (2001) in The Metabolic and Molecular Bases of Inherited Disease, eds. Scriver, C. R., Beaudet, A. L., Sly, W. S., & Valle, D. (McGraw-Hill, New York), pp. 3421-3451.

2. Nelson, A., Peterson L., Frampton B., Sly, W. S.(1982) J. Pediatr. 101:574.

3. Gheti, V., Ward, E. S., (2000). Multiple Roles for the Major Histocompatibility Complex Class I-Related Receptor FcRn. Annu. Rev. Immunol. 18:739-766.

4. Niwa, H., Yamnamura, K., Miyazaki, J. (1991) Efficient selection for high-expression transfectants with a novel eukaryotic vector. Gene 108, 193-200.

5. Chinese Hamster Ovary Cell Line American Type Culture Collection, ATCC CRL 9618.

6. Ulmasov, B., Waheed, A., Shah, G. N., Grubb, J. H., Sly, W. S., Tu, C., Silverman, D. N. (2000) Purification and kinetic analysis of recombinant CAXII, a membrane carbonic anhydrase overexpressed in certain cancers. PNAS 97(26) 14212-14217.

7. Glaser, J. H. and Sly, W. S. (1973). Beta-glucuronidase deficiency mucopolysaccharidosis: methods for enzymatic diagnosis. J. Lab. Clin. Med. 82: 969-977.

8. Islam, M. R., Grubb, J. H. and Sly, W. S. (1993). C-terminal Processing of Human β-glucuronidase J. Biol. Chem. 268(30):22627-22633.

9. Laemmli, U. K., (1970) Nature (London) 227, 680-685.

10. von Figura, K., and Hasilik, A. (1986). Lysosomal enzymes and their receptors. Annu. Rev. Biochem. 55: 167-193.

11. LeBowitz, J. H., Grubb, J. H., Maga, J. A., Schmiel, D. H., Vogler, C. and Sly, W. S. (2004). Glycosylation-independent targeting enhances enzyme delivery to lysosomes and decreases storage in mucopolysaccharidosis type VII mice. Proc. Natl. Acad. Sci. USA 101: 3083-3088.

12. Vogler, C., Grubb, J. H., Levy, B., Galvin, N., Tan, Y., Nishioka T., Tomatsu, S., Isele, C. and Sly, W. S. Defining the individual roles of the mannose 6-phosphate and the mannose receptors in enzyme therapy in the mannose receptor null mucopolysaccharidosis VII mouse. Manuscript in preparation.

13. Hickman, S., Shapiro, L. J., and Neufeld, E. F. (1974). A recognition marker required for uptake of a lysosomal enzyme by cultured fibroblasts. BBRC 57, Issue 1, 55-61.

14. Orii, K. O., Grubb, J. H., Vogler, C., Levy, B., Tan, Y., Markova K., Davidson, B. L., 15. Orii, T., Kondo, N., and Sly, W. S. (2005). Defining the pathway for Tat-mediated delivery of beta-glucuronidase in cultured cells and MPS VII mice. Molecular Therapy 12, 2, 345-352.

SUMMARY OF THE INVENTION

The inventors have made the surprising discovery that polypeptides that are linked to an immunoglobulin fraction-crystalizable domain (Fc-domain) are able to cross the placenta and to enter the circulation of the fetus. Thus an object of the invention is a composition of matter comprising a polypeptide linked to a Fc-domain. Preferred polypeptides have a therapeutic use, such as a metabolic enzyme. More preferred polypeptides are enzymes related to lysosomal storage. A most preferred polypeptide is a mucopolysaccharidosis-related enzyme, such as for example beta-glucuronidase (GUS).

Another object of the invention is a system or kit for the delivery of an agent across the placenta, comprising (a) a chimeric polypeptide having a Fc-domain and a therapeutic domain and (b) a pharmaceutical excipient. In a preferred embodiment, the therapeutic domain contains a polypeptide having therapeutic value, such as an enzyme useful in enzyme replacement therapy. More preferably, the therapeutic domain has enzyme activity related to lysosomal storage.

Most preferably the therapeutic domain has mucopolysaccharidosis-related enzyme activity, such as for example beta-glucuronidase (GUS).

Another object of the invention is a method for treating an inborn error of metabolism in a fetus comprising administering a therapeutically effective amount of a chimeric polypeptide. Administration may be by any route, preferably intravenous administration of a chimeric peptide in an pharmaceutical excipients. Inborn errors of metabolism comprise diseases such as lysosomal storage diseases, which include MPS diseases, such as MPS VII. The chimeric polypeptide has a therapeutic domain and a Fc-domain as described herein.

BRIEF DESCRIPTION OF THE SEVERAL VIEWS OF THE DRAWING

FIG. 1 is a schematic drawing showing GUS-Fc constructions in mammalian expression vector pCXN;

FIG. 2 is a schematic drawing showing a top view of SDS-PAGE results for purified GUS and GUS-Fc;

FIG. 3 is a graph showing the clearance of infused GUSB, GUSB-Fc or Periodate-treated GUS B from the plasma of MR+/+ or MR−/− mice; and FIG. 4 is a schematic drawing showing a top view of clearance of storage in tissues from pups delivered from moms infused with GUS-FC on embryonic days 17 and 18.

DETAILED DESCRIPTION OF THE INVENTION

Applicants have discovered that the prenatal delivery of a chimeric protein containing the IgG Fc-domain (GenBank Accession No. X68090), which after infusion into the maternal circulation, mediates delivery of the protein across the placenta into the circulation of the fetus. Specifically, applicants have invented a B-glucuronidase/Fc chimeric protein and used it for prenatal enzyme replacement therapy in the MPS VII mouse. The chimeric enzyme, after intravenous infusion into the pregnant female on embryonic days 17 and 18, was delivered across the placenta utilizing the interaction between the Fc tag and the neonatal Fc receptor(FcRn). This enzyme was transported into the circulation of the fetuses, and due to the presence of the M6P recognition marker on the enzyme, was taken up by the M6P-receptor and delivered to the lysosomes of numerous tissues. Here it was able to clear lysosomal storage material characteristic for this disease.

Applicants have shown that the invention can be applied to the prenatal treatment of MPS VII and certainly could be expanded to prenatally treat any of the numerous lysosomal storage diseases. However, it is envisioned that the invention can be used to deliver any protein, peptide, drug or therapeutic across the placenta to the fetus.

Thus, in one embodiment, the invention is directed to a chimeric protein in which human GUS contains a carboxy terminal tag consisting of the CH2-CH3 domain of human IgG. This chimera is an active form of B-glucuronidase containing the M6P lysosomal targeting signal. When this chimera was intravenously infused into a pregnant mouse, the Fc domain mediates transport across the placenta into the circulation of the fetus. From there, the enzyme was taken up via the M6P receptor present in the tissues of the fetus and delivered to the lysosomes of those tissues. Enzyme delivered in this manner was able to clear accumulated glycosaminoglycans from the lysosomes of the MPS VII knock-out mouse.

Applicants have used the MPS VII mouse model to provide proof-of-concept for this transplacental delivery system. One skilled in the art would reasonably expect that this method can be used in any and all lysosomal storage diseases that are amenable to enzyme replacement therapy. Applicants further envision that the instant Fc delivery system can be used to deliver many other therapeutic proteins, peptides and biologics across the placenta.

In another embodiment, the invention is directed to systems and methods for delivery therapeutic polypeptides across the placenta and into the fetus. Preferably (but not limited to) an object of this invention is to deliver corrective enzyme to a MPS VII fetus by infusing a chimeric enzyme containing the Fc domain from human IgG fused to the c-terminus of recombinant human GUS into the pregnant mother. To test this hypothesis, the c-terminal fusion protein GUS-Fc was compared to native phosphorylated recombinant GUS (PGUS) for clearance from the murine maternal circulation, delivery to the fetus and reduction of lysosomal storage. (The murine system is used experimentally to model the human, hence the invention is broadly applicable to any and all mammals, most preferably humans.) After administering the GUS-Fc enzyme (4-6 mg/kg) to the pregnant mother on gestational days 17 and 18, Applicants found clear evidence that the GUS-Fc was transported across the placenta. Enzyme activity was present in newborn MPS VII (mps −/−) mice plasma at 2000-5000 U/ml, 1000 times more than background levels (2-5 U/ml) seen following administration of non-Fc tagged enzyme, which was not detectably transported. These elevated levels in treated(mps −/−) newborn mice were roughly 100 times those seen in untreated wild type newborns. Reduction of lysosomal storage in storage in heart valves, liver and spleen provided evidence that the administered GUS-Fc was corrective in the MPS VII fetus.

Generation of Stable Cell Lines Secreting GUS and GUS-FC.

Using DNA cloning techniques Applicants added the cDNA sequence encoding the CH2-CH3 domains of human Immunoglobulin G(Genbank Accession #) to the carboxy terminus of the fall length cDNA for human B-glucuronidase (Genbank Accession # NM_000181)(GUS-Fc, FIG. 1). The polynucleotide sequence is set forth in SEQ ID NO:1 and its corresponding polypeptide sequence is set forth in SEQ ID NO:2, which are incorporated herein. Both the wild type and Fc-tagged cDNAs were subcloned into the mammalian expression vector pCXN.(4) This expression vector contains an expression cassette consisting of the chicken beta-actin promoter coupled to the CMV Intermediate-early(CMV-IE) enhancer. pCXN also contains a selectable marker for G418 allowing selection of stably expressing mammalian cells.

These plasmids were introduced into the Chinese hamster ovary cell line, CHO-K1(5) by electroporation(6). After selection in growth medium consisting of Minimal Essential Medium +35 µg/ml proline +15% fetal bovine serum(FBS) +400 µg G418, colonies were picked and grown to confluency in 48-well plates. High level expressing clones were identified by measuring GUS activity secreted into the conditioned medium from these clones(ref). The highest-producing clone was scaled up and secreted enzyme was collected in low serum collection medium consisting of Waymouth MB 752/1+2% FBS. Conditioned medium collected in this way was pooled, centrifuged at 5000× g for 20 minutes and the supernatant was collected and frozen at −20° F. until sufficient quantities were accumulated for purification.

Measurement of GUS Activity

GUS activity was measured using the 10 mM 4-methylumbelliferyl β-D-glucuronide as substrate in 0.1M sodium acetate buffer pH 4.8, 1 mg/ml crystalline BSA as previously described (7).

Purification of GUS and GUS-Fc

Affinity chromatography procedure was essentially as described(8). Conditioned medium from CHO cells overexpressing the GUS or GUS-Fc fusion protein was filtered through a 0.22μ filter. Sodium chloride (crystalline) was added to a final concentration of 0.5M, and sodium azide was added to a final concentration of 0.025% by adding 1/400 volume of a 10% stock solution. The medium was applied to a 5 mL column of anti-human β-glucuronidase-Affigel 10 (pre-equilibrated with Antibody Sepharose Wash Buffer: 10 mM Tris pH 7.5, 10 mM potassium phosphate, 0.5 M NaCl, 0.025% sodium azide) at a rate of 25 mL/hour at 4° C. The column was washed at 36 mL/hour with 10-20 column volumes of Antibody Sepharose Wash Buffer. The column was eluted at 36 mL/hour with 50 mL of 10 mM sodium phosphate pH 5.0+3.5 M $MgCl_2$. 4 mL fractions were collected and assayed for GUS activity. Fractions containing the fusion protein were pooled, diluted with an equal volume of P6 buffer (25 mM Tris pH 7.5, 1 mM β-glycerol phosphate, 0.15 mM NaCl, 0.025% sodium azide) and desalted over a BioGel P-6 column (pre-equilibrated with P6 buffer) to remove the $MgCl_2$ and to change the buffer to P6 buffer for storage. The fusion protein was eluted with P6 buffer, fractions containing GUS activity were pooled and assayed for GUS activity and protein. Both purified GUS and GUS-Fc were stored frozen at −80° C. in P6 buffer for long-term stability. For mouse infusions, the enzymes were highly concentrated in Centricon YM-30 concentrators and the buffer was changed to P6 Buffer without azide. These concentrates were frozen in small aliquots at −80° C. until use.

Characterization of Purified GUS and GUS-Fc.

GUS is a 300 KDa protein that exists as a homotetramer consisting of four identical monomers of apparent molecular weight of 75 KDa. In FIG. 2, two different amounts of purified GUS were analyzed by SDS-PAGE under reducing conditions(9). The apparent molecular weight is 75 KDa as expected. When GUS-Fc was analyzed by SDS-PAGE the apparent molecular weight as seen below is approximately 104 KDa indicating an increase of ~29 KDa. The addition of the Fc domain would be expected to add approximately 29 KDa to the GUS monomer. There is a small amount of 75 KDa protein present also which might indicate a small percentage of protein from which the Fc domain has been removed by proteolysis.

The addition of the Fc domain to GUS would not only confer the ability to bind to the FcRn, but should also allow the binding to the bacterial Protein G. Protein G immobilized on various resins have long been used to precipitate IgG/antigen complexes during immunoprecipitation reactions. This technique can be used to analyze the proportion of GUS-Fc that contains a functional Fc domain quite easily. Only protein that contains functional Fc will be precipitated by immobilized Protein G. In this case, the GUS activity serves as the reporter in the assay. Briefly, 500 units of GUS or GUS-Fc were combined with Protein G-Sepharose in phosphate buffered saline(PBS) pH 7.4, 1 mg/ml crystalline bovine serum albumin(C-BSA). This reaction mixture was mixed by rotation for 4 hours at 4° C. After centrifugation at 10,000×g for 2 minutes, the supernatant was removed and saved for assay. The pellets were washed 2 times with 1 ml each of PBS then resuspended in 1 ml of PBS+C-BSA. As shown in Table I, only 5% of wild type GUS was precipitated by Protein G-Sepharose when analyzed in this manner. This is considered to be in the range of non-specific binding to the resin. In contrast, both unpurified GUS-Fc from the secretion medium and purified GUS-Fc were precipitated 85% and 74%, respectively by Protein G-Sepharose. These results indicate that the Fc domain on the fusion protein does confer the ability to function similar to the Fc domain on IgG. They also indicate the majority of the purified GUS-Fc seems to contain a functional Fc domain.

Eventual delivery of any lysosomal enzyme to the lysosome requires the presence of the mannose 6-phosphate (M6P) recognition signal on the enzyme. This signal is recognized by two separate mannose 6-phosphate receptors that can mediate delivery of the lysosomal enzyme to the lysosome(10). Postranslational modification of lysosomal enzymes is required to add M6P to their N-linked oligosaccharides. This process is accomplished by a two-step procedure utilizizing the UDP-GlcNac lysosomal phosphotransferase which transfers GlcNAc—$PO_4$ to terminal mannose residues on the oligosaccharides. The second step utilizes the phosphodiesterase(UCE) that removes the GlcNAc cap exposes the M6P. With previous GUS fusion proteins Applicants have made, Applicants have seen various reductions in the M6P content. Applicants attribute this to some steric or conformational change induced by the addition of the fusion tag that affects the efficiency of either the phosphotransferase or UCE to produce a functional M6P recognition signal.

In order to assess the amount of M6P recognition signal that GUS Fc contains relative to GUS, Applicants measured the rate at which the enzyme is taken up by human fibroblasts (11). Human fibroblasts contain mannose 6-phosphate receptors on their cell surfaces which mediate the endocytosis of M6P-containing ligands. Table 1 shows the results of an uptake experiment in which 8000 units of GUS or GUS Fc were added to the medium of human fibroblasts in the presence and absence of 2 mM M6P. Results are expressed as M6P specific enzyme uptake per mg of cell protein per hour of uptake at 37° C.

As can be seen, GUS is taken up quite well in a M6P-specific manner. However, the uptake of GUS-Fc is reduced to about 14% of that seen for GUS. Even though this reduction is significant, the enzyme still has the ability to be delivered to lysosomes by the M6P receptor.

Mouse Infusion Experiments

In addition to mediating transplacental transfer, it has been well documented that the Fc domain is responsible for maintaining high levels of IgG in the circulation. The FcRn, which is also expressed in endothelial cells in adults recaptures IgG which has been endocytosed or pinocytosed out of the circulation. The FcRn which resides in the endosomes binds the Fc moiety at IgG at an acid pH in the endosome and transports it back out into the circulation. This has the net effect of returning IgG that would normally be delivered to lysosomes and degraded, back into the circulation.

Because of this, one skilled in the art would predict that GUS-Fc, which would normally be rapidly cleared from the circulation by mannose and M6P-receptors, would be recaptured and returned to the circulation. This would have the net effect of prolonging the clearance times and maintaining higher levels of GUS-Fc in the circulation for a longer time. This should increase the opportunity for GUS-Fc to be recognized by FcRn receptors in the placenta and thus increase the amount of enzyme transported across to the fetus.

In order to test these hypotheses, FIG. 3 shows the clearance from the circulation in either mannose receptor positive MPS VII mice(MR +/+) or mannose receptor negative MPS VII mice(MR −/−) (12). Untagged GUS is cleared fairly rapidly from MR +/+ mice as one would expect. The same enzyme, when infused into the MR −/− mouse is cleared significantly more slowly as it is being cleared only by the M6P receptor. In contrast, GUS-Fc is cleared substantially less slowly in both the MR +/+ and MR −/− mice. Applicants also tested GUS that had been treated with periodate and borohydride(PB-GUS) which destroys all carbohydrate on the enzyme(13). Since PB-GUS is no longer a ligand for either the mannose or M6P receptors its clearance time should be extremely prolonged. As seen in FIG. 3, the clearance of PB-GUS is extremely low during the time frame of these experiments. These results would indicate that the Fc domain is functional and is able mediate recapture of GUS-Fc by FcRn. This also makes it highly likely, that the Fc domain on GUS-Fc would mediate binding to the FcRn in the placenta and therefore transcytosis of the tagged enzyme across the placenta into the fetal circulation.

In order to test for transplacental transport of GUS-Fc Applicants did the experiments summarized in Table 2. Timed pregnancies were set up using either MR+/+ or MR−/− females. On calculated Embryonic days 17 and 18, these pregnant mice were infused with 380,000 units of GUS, GUS-Fc, PB-GUS or PBS by bolus infusion into the tail vein. Pups that were delivered, that were later analyzed by PCR to confirm their homozygous status) were collected on Newborn Day 1, sacrificed and blood collected. After centrifugation, plasma was collected and assayed for B-glucuronidase as described above. Both MR +/+ and MR −/− mice infused with PBS had very low levels consistant with being B-glucuronidase deficient. Similarly, both types of mice have low levels of enzyme when the mothers had bee infused with untagged GUS. In contrast, pups from both the MR +/+ and MR −/− pregnant females infused with GUS-Fc contained highly elevated levels of enzyme in their plasma. This could only be attributed to transplacental transport of the Fc-tagged enzyme. The levels in the pups from the MR −/− moms are about 2-fold higher than from the MR +/+ moms. This would seem to correlate with differences in clearance rates from the circulation in the pregnant females.

The next question Applicants asked was if the GUS-Fc could be delivered to tissues of the fetus once it had been delivered into the fetal circulation. Two lines of evidence support this. The first is summarized in Table 3 below. Tissues were collected from the pups after perfusion to remove any enzyme still contained in the blood. The tissues were homogenized and assayed for B-glucuronidase and protein(14). Enzyme levels are expressed as units/mg protein. Enzyme levels were compared to wild type B6 pups that were harvested in the same way. As can be seen, pups from pregnant mice that had been infused with untagged GUS were very low, essentially the same as for pups from non-infused pregnant mice. However, pups from pregnant mice infused with GUS-Fc contained significant amounts of activity in many tissues. While these levels are not nearly as high as in wild type pups, they are close to the 5-10% of normal levels which have been documented to be clinically effective in treating this disease.

The second line of evidence that enzyme has been delivered to the fetal tissues is presented in FIG. 4. Lysosomes in untreated MPS VII mice accumulate undegraded glycosaminylglycans and become distended in appearance. These distended lysosomes are evident in spleen, liver and heart from pups from untreated MPS VII mice shown in the first column of FIG. 4. In contrast, the same tissues from pups from both MR −/− and MR +/+ females treated with GUS-Fc, showed substantial clearance in the former and partial clearance in the latter. This is considered definitive proof that GUS-Fc infused into the pregnant female was able to cross the placenta and to ultimately be delivered to the lysosomes in tissues of the fetuses.

TABLE 1

Analysis of GUS and GUS-Fc For Functional Fc and M6P Recognition Signal

| Enzyme | % of Enzyme Preciptated By Protein G Sepharose | M6P-Specific Uptake By Fibroblasts Units/mg/hr |
|---|---|---|
| GUS | 5 | 433 |
| GUS-Fc Medium | 85 | — |
| GUS-Fc Purified | 74 | 60 |

TABLE 2

Plasma GUS Activity In Pups On Newborn Day 1 After GUS, GUS Fc or PB-GUS Infusion Into Pregnant MR +/+ vs MR −/− Females On Embryonic Days 17 & 18

| Condition | Total # Moms | Total # Pups | Plasma GUS Level Pups NB Day 1 |
|---|---|---|---|
| MR +/+ +PBS | 2 | 2 | 2.5 ± 2.5 |
| MR +/+ +GUS | 2 | 6 | 4.5 ± 4.8 |
| MR +/+ +GUS-Fc | 2 | 10 | 2166 ± 802 |
| MR −/− +PBS | 2 | 6 | 2.4 ± 1.4 |
| MR −/− +GUS | 1 | 6 | 2.93 ± 0.99 |
| MR −/− +GUS-Fc | 7 | 17 | 4927 ± 2110 |
| MR −/− PB-GUS | 2 | 8 | 15 ± 8.7 |

TABLE 3

GUS Levels In Perfused Tissues From Newborn MR +/+ or MR −/− Pups After Transplacental Delivery On ED 17 and 18

| Tissue | B6 Non Infused | Non Infused | MR +/+ GUS Infused | MR +/+ GUS-Fc Infused | MR −/− Non Infused | MR −/− GUS Infused | MR −/− GUS-Fc Infused | PB-GUS Infused |
|---|---|---|---|---|---|---|---|---|
| Brain | 28.0 ± 1.2 | 0.03 ± 0.03 | n.d. | 0.14 ± 0.05 | 0.11 ± 0.04 | 0.14 ± 0.10 | 2.70 ± 1.80 | 0.09 ± 0.02 |
| Liver | 207 ± 1.0 | 0.13 ± 0.13 | 0.40 ± 0.20 | 3.27 ± 0.98 | 0.04 ± 0.02 | 0.04 ± 0.01 | 7.82 ± 1.71 | 0.13 ± 0.05 |
| Spleen | 369 ± 86 | 0.025 ± 0.036 | n.d. | 0.39 ± 0.37 | 0.09 ± 0.05 | 0.18 ± 0.27 | 3.80 ± 1.10 | 0.12 ± 0.23 |
| Heart | 107 ± 0.5 | 0.04 ± 0.07 | n.d. | 1.05 ± 0.49 | 0.08 ± 0.07 | 0.05 ± 0.04 | 14.43 ± 4.24 | 0.13 ± 0.04 |
| Kidney | 223 ± 4.0 | 0.17 ± 0.06 | n.d. | 0.74 ± 0.4 | 0.06 ± 0.04 | 0.06 ± 0.01 | 4.81 ± 0.68 | 0.20 ± 0.14 |
| Lung | 186 ± 12 | 0.07 ± 0.02 | n.d. | 0.70 ± 0.30 | 0.06 ± 0.01 | 0.07 ± 0.01 | n.d. | n.d. |
| Eye | n.d. | 0.21 ± 0.13 | n.d. | 1.00 ± 0.52 | 0.38 ± 0.13 | 0.10 ± 0.07 | 6.39 ± 1.36 | n.d. |
| | n = 2 | n = 6 | n = 4 | n = 8 | n = 6 | n = 6 | n = 4 | n = 9 |

What is claimed:

1. A composition comprising the polypeptide as set forth in SEQ ID NO:2.

2. The composition of claim 1 further comprising a mucopolysaccharide enzyme.

3. The composition of claim 2 wherein the mucopolysaccharide enzyme is a beta-glucuronidase.

4. A method for treating MPS VII in a fetus or embryo comprising the step of delivering a fusion protein having a sequence as set forth in SEQ ID NO:2 to a pregnant mother, wherein the fusion protein comprises a Fc fragment of an IgG and a mucopolysaccharide enzyme, and wherein the fusion protein crosses the placenta and enters the fetal blood stream, and wherein the fusion protein is taken up into fetal tissue such that the mucopolysaccharide enzyme restores normal metabolic activity in the fetus.

* * * * *

UNITED STATES PATENT AND TRADEMARK OFFICE
CERTIFICATE OF CORRECTION

| | | |
|---|---|---|
| PATENT NO. | : 7,871,624 B2 | Page 1 of 1 |
| APPLICATION NO. | : 11/769693 | |
| DATED | : January 18, 2011 | |
| INVENTOR(S) | : Jeffrey H. Grubb | |

It is certified that error appears in the above-identified patent and that said Letters Patent is hereby corrected as shown below:

Col. 2, line 4, delete "Yamnamura" and replace with -- Yamamura --

Col. 4, line 37, delete "fail" and replace with -- full --

Signed and Sealed this
Twenty-ninth Day of March, 2011

David J. Kappos
*Director of the United States Patent and Trademark Office*

SEQUENCE LISTING

<160> NUMBER OF SEQ ID NOS: 2

<210> SEQ ID NO 1
<211> LENGTH: 2713
<212> TYPE: DNA
<213> ORGANISM: Artificial
<220> FEATURE:
<223> OTHER INFORMATION: Synthetic Chimera

<400> SEQUENCE: 1

```
ggtggccgag cggggaccg ggaagcatgg cccggggtc ggcggttgcc tgggcggcgc        60
tcgggccgtt gttgtgggc tgcgcgctgg ggctgcaggg cgggatgctg taccccagg       120 agagcccgtc gcgggagtgc aaggagctgg acggcctctg gagcttccgc gccgacttct     180
ctgacaaccg acgccggggc ttcgaggagc agtggtaccg gcggccgctg tgggagtcag     240
gccccaccgt ggacatgcca gttccctcca gcttcaatga catcagccag gactggcgtc     300
tgcggcattt tgtcggctgg gtgtggtacg aacgggaggt gatcctgccg gagcgatgga     360
cccaggacct gcgcacaaga gtggtgctga ggattggcag tgcccattcc tatgccatcg     420
tgtgggtgaa tgggtcgac acgctagagc atgagggggg ctacctcccc ttcgaggccg     480
acatcagcaa cctggtccag gtgggcccc tgccctcccg gctccgaatc actatcgcca     540
tcaacaacac actcacccc accaccctgc caccagggac catccaatac ctgactgaca     600
cctccaagta tcccaagggt tactttgtcc agaacacata ttttgacttt ttcaactacg     660
ctggactgca gcggtctgta cttctgtaca cgacacccac cctacatc gatgacatca      720 ccgtcaccac cagcgtggag caagacagtg ggctggtgaa ttaccagatc tctgtcaagg     780
gcagtaacct gttcaagttg gaagtgcgtc ttttggatgc agaaaacaaa gtcgtggcga     840
atgggactgg gacccaggc caacttaagg tgccaggtgt cagcctctgg tggccgtacc     900
tgatgcacga acgccctgcc tatctgtatt cattggaggt gcagctgact gcacagacgt     960
cactggggcc tgtgtctgac ttctacacac tccctgtggg gatccgcact gtggctgtca    1020
ccaagagcca gttcctcatc aatgggaaac cttctctatt tccacggtgtc aacaagcatg   1080 aggatgcgga catccgaggg aagggcttcg actggcgct gctggtgaag gacttcaacc     1140
tgcttcgctg gcttggtgcc aacgcttcc gtaccagcca ctaccccat gcagaggaag      1200 tgatgcagat gtgtgaccgc tatgggattg tggtcatcga tgagtgtccc ggcgtgggcc    1260
tggcgctgcc gcagttcttc aacaacgttt ctctgcatca ccacatgcag gtgatggaag    1320
aagtggtgcg tagggacaag aaccaccccg cggtcgtgat gtggtctgtg gccaacgagc    1380
ctgcgtccca cctagaatct gctggctact acttgaagat ggtgatcgct cacaccaaat    1440
ccttggaccc ctcccggcct gtgacctttg tgagcaactc taactatgca gcagacaagg    1500
gggctccgta tgtggatgtg atctgtttga acagctacta ctcttggtat cacgactacg    1560
ggcacctgga gttgattcag ctgcagctgg ccacccagtt tgagaactgg tataagaagt    1620
atcagaagcc cattattcag agcgagtatg gagcagaaac gattgcaggg tttcaccagg    1680
atccacctct gatgttcact gaagagtacc agaaagtct gctagagcag taccatctgg    1740
gtctggatca aaacgcaga aaatatgtgg ttggagagct catttggaat tttgccgatt     1800
tcatgactga acagtcaccg acgagagtgc tgggaataa aaggggatc ttcactcggc     1860 agagacaacc aaaaagtgca gcgttccttt tgcgagagag atactggaag attgccaatg    1920
aaaccaggta tccccactca gtagccaagt cacaatgttt ggaaaacagc ccgtttactg    1980
```

```
gcggaggtgg caccggtatg gcacctgaac tcctgggggg accgtcagtc ttcctcttcc   2040
ccccaaaacc caaggacacc ctcatgatct cccggacccc tgaggtcaca tgcgtggtgg   2100
tggacgtgag ccacgaagac cctgaggtca agttcaactg gtacgtggac ggcgtggagg   2160
tgcataatgc caagacaaag ccgcgggagg agcagtacaa cagcacgtac cgtgtggtca   2220
gcgtcctcac cgtcctgcac caggactggc tgaatggcaa ggagtacaag tgcaaggtct   2280
ccaacaaagc cctcccagcc cccatcgaga aaaccatctc caaagccaaa gggcagcccc   2340
gagaaccaca ggtgtacacc ctgcccccat cccgggagga gatgaccaag aaccaggtca   2400
gcctgacctg cctggtcaaa ggcttctatc ccagcgacat cgccgtggag tgggagagca   2460
atgggcagcc ggagaacaac tacaagacca cgcctcccgt gctggactcc gacggctcct   2520
tcttcctcta tagcaagctc accgtggaca agagcaggtg gcagcagggg aacgtcttct   2580
catgctccgt gatgcatgag gctctgcaca accactacac gcagaagagc ctctccctgt   2640
ccccggagct gcaactggag gagagctgtg ctgaggccca ggacggggag ctggacgggc   2700
tctggacgac tga                                                     2713
```

<210> SEQ ID NO 2
<211> LENGTH: 903
<212> TYPE: PRT
<213> ORGANISM: Artificial
<220> FEATURE:
<223> OTHER INFORMATION: Synthetic Chimera

<400> SEQUENCE: 2

```
Trp Pro Ser Gly Gly Pro Gly Ser Met Ala Arg Gly Ser Ala Val Ala
1               5                   10                  15

Trp Ala Ala Leu Gly Pro Leu Leu Trp Gly Cys Ala Leu Gly Leu Gln
                20                  25                  30

Gly Gly Met Leu Tyr Pro Gln Glu Ser Pro Ser Arg Glu Cys Lys Glu
            35                  40                  45

Leu Asp Gly Leu Trp Ser Phe Arg Ala Asp Phe Ser Asp Asn Arg Arg
        50                  55                  60

Arg Gly Phe Glu Glu Gln Trp Tyr Arg Arg Pro Leu Trp Glu Ser Gly
65                  70                  75                  80

Pro Thr Val Asp Met Pro Val Pro Ser Ser Phe Asn Asp Ile Ser Gln
                85                  90                  95

Asp Trp Arg Leu Arg His Phe Val Gly Trp Val Trp Tyr Glu Arg Glu
            100                 105                 110

Val Ile Leu Pro Glu Arg Trp Thr Gln Asp Leu Arg Thr Arg Val Val
        115                 120                 125

Leu Arg Ile Gly Ser Ala His Ser Tyr Ala Ile Val Trp Val Asn Gly
    130                 135                 140

Val Asp Thr Leu Glu His Glu Gly Gly Tyr Leu Pro Phe Glu Ala Asp
145                 150                 155                 160

Ile Ser Asn Leu Val Gln Val Gly Pro Leu Pro Ser Arg Leu Arg Ile
                165                 170                 175

Thr Ile Ala Ile Asn Asn Thr Leu Thr Pro Thr Thr Leu Pro Pro Gly
            180                 185                 190

Thr Ile Gln Tyr Leu Thr Asp Thr Ser Lys Tyr Pro Lys Gly Tyr Phe
        195                 200                 205

Val Gln Asn Thr Tyr Phe Asp Phe Phe Asn Tyr Ala Gly Leu Gln Arg
    210                 215                 220
```

```
Ser Val Leu Leu Tyr Thr Thr Pro Thr Thr Tyr Ile Asp Asp Ile Thr
225                 230                 235                 240
Val Thr Thr Ser Val Glu Gln Asp Ser Gly Leu Val Asn Tyr Gln Ile
                245                 250                 255
Ser Val Lys Gly Ser Asn Leu Phe Lys Leu Glu Val Arg Leu Leu Asp
            260                 265                 270
Ala Glu Asn Lys Val Val Ala Asn Gly Thr Gly Thr Gln Gly Gln Leu
            275                 280                 285
Lys Val Pro Gly Val Ser Leu Trp Trp Pro Tyr Leu Met His Glu Arg
            290                 295                 300
Pro Ala Tyr Leu Tyr Ser Leu Glu Val Gln Leu Thr Ala Gln Thr Ser
305                 310                 315                 320
Leu Gly Pro Val Ser Asp Phe Tyr Thr Leu Pro Val Gly Ile Arg Thr
                325                 330                 335
Val Ala Val Thr Lys Ser Gln Phe Leu Ile Asn Gly Lys Pro Phe Tyr
                340                 345                 350
Phe His Gly Val Asn Lys His Glu Asp Ala Asp Ile Arg Gly Lys Gly
            355                 360                 365
Phe Asp Trp Pro Leu Leu Val Lys Asp Phe Asn Leu Leu Arg Trp Leu
370                 375                 380
Gly Ala Asn Ala Phe Arg Thr Ser His Tyr Pro Tyr Ala Glu Glu Val
385                 390                 395                 400
Met Gln Met Cys Asp Arg Tyr Gly Ile Val Val Ile Asp Glu Cys Pro
                405                 410                 415
Gly Val Gly Leu Ala Leu Pro Gln Phe Phe Asn Asn Val Ser Leu His
            420                 425                 430
His His Met Gln Val Met Glu Glu Val Val Arg Arg Asp Lys Asn His
            435                 440                 445
Pro Ala Val Val Met Trp Ser Val Ala Asn Glu Pro Ala Ser His Leu
450                 455                 460
Glu Ser Ala Gly Tyr Tyr Leu Lys Met Val Ile Ala His Thr Lys Ser
465                 470                 475                 480
Leu Asp Pro Ser Arg Pro Val Thr Phe Val Ser Asn Ser Asn Tyr Ala
                485                 490                 495
Ala Asp Lys Gly Ala Pro Tyr Val Asp Val Ile Cys Leu Asn Ser Tyr
            500                 505                 510
Tyr Ser Trp Tyr His Asp Tyr Gly His Leu Glu Leu Ile Gln Leu Gln
            515                 520                 525
Leu Ala Thr Gln Phe Glu Asn Trp Tyr Lys Lys Tyr Gln Lys Pro Ile
            530                 535                 540
Ile Gln Ser Glu Tyr Gly Ala Glu Thr Ile Ala Gly Phe His Gln Asp
545                 550                 555                 560
Pro Pro Leu Met Phe Thr Glu Glu Tyr Gln Lys Ser Leu Leu Glu Gln
                565                 570                 575
Tyr His Leu Gly Leu Asp Gln Lys Arg Arg Lys Tyr Val Val Gly Glu
                580                 585                 590
Leu Ile Trp Asn Phe Ala Asp Phe Met Thr Glu Gln Ser Pro Thr Arg
            595                 600                 605
Val Leu Gly Asn Lys Lys Gly Ile Phe Thr Arg Gln Arg Gln Pro Lys
            610                 615                 620
Ser Ala Ala Phe Leu Leu Arg Glu Arg Tyr Trp Lys Ile Ala Asn Glu
625                 630                 635                 640
Thr Arg Tyr Pro His Ser Val Ala Lys Ser Gln Cys Leu Glu Asn Ser
```

-continued

```
                        645                 650                 655
Pro Phe Thr Gly Gly Gly Thr Gly Met Ala Pro Glu Leu Leu Gly
                660                 665                 670

Gly Pro Ser Val Phe Leu Phe Pro Pro Lys Pro Lys Asp Thr Leu Met
            675                 680                 685

Ile Ser Arg Thr Pro Glu Val Thr Cys Val Val Val Asp Val Ser His
        690                 695                 700

Glu Asp Pro Glu Val Lys Phe Asn Trp Tyr Val Asp Gly Val Glu Val
705                 710                 715                 720

His Asn Ala Lys Thr Lys Pro Arg Glu Glu Gln Tyr Asn Ser Thr Tyr
                725                 730                 735

Arg Val Val Ser Val Leu Thr Val Leu His Gln Asp Trp Leu Asn Gly
            740                 745                 750

Lys Glu Tyr Lys Cys Lys Val Ser Asn Lys Ala Leu Pro Ala Pro Ile
            755                 760                 765

Glu Lys Thr Ile Ser Lys Ala Lys Gly Gln Pro Arg Glu Pro Gln Val
        770                 775                 780

Tyr Thr Leu Pro Pro Ser Arg Glu Glu Met Thr Lys Asn Gln Val Ser
785                 790                 795                 800

Leu Thr Cys Leu Val Lys Gly Phe Tyr Pro Ser Asp Ile Ala Val Glu
            805                 810                 815

Trp Glu Ser Asn Gly Gln Pro Glu Asn Asn Tyr Lys Thr Thr Pro Pro
                820                 825                 830

Val Leu Asp Ser Asp Gly Ser Phe Phe Leu Tyr Ser Lys Leu Thr Val
            835                 840                 845

Asp Lys Ser Arg Trp Gln Gln Gly Asn Val Phe Ser Cys Ser Val Met
        850                 855                 860

His Glu Ala Leu His Asn His Tyr Thr Gln Lys Ser Leu Ser Leu Ser
865                 870                 875                 880

Pro Glu Leu Gln Leu Glu Glu Ser Cys Ala Glu Ala Gln Asp Gly Glu
                885                 890                 895

Leu Asp Gly Leu Trp Thr Thr
                900
```